US011103655B2

(12) United States Patent
Schneider

(10) Patent No.: US 11,103,655 B2
(45) Date of Patent: *Aug. 31, 2021

(54) HANDHELD APPARATUS FOR VAPORIZATION OF PLANT-BASED OR SYNTHETIC COMPOUNDS BY LASER

(71) Applicant: LUMENARY, INC., Petaluma, CA (US)

(72) Inventor: Robert Schneider, Bodega Bay, CA (US)

(73) Assignee: Lumenary, Inc., Petaluma, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/860,280

(22) Filed: Apr. 28, 2020

(65) Prior Publication Data
US 2020/0253278 A1    Aug. 13, 2020

Related U.S. Application Data

(63) Continuation of application No. 15/553,980, filed as application No. PCT/IB2016/001166 on Feb. 24, 2016, now Pat. No. 10,667,556.

(Continued)

(51) Int. Cl.
*A61M 11/04* (2006.01)
*A61M 15/06* (2006.01)
(Continued)

(52) U.S. Cl.
CPC .......... *A61M 11/041* (2013.01); *A24F 40/40* (2020.01); *A24F 40/42* (2020.01); *A24F 40/46* (2020.01);
(Continued)

(58) Field of Classification Search
CPC ...... A61M 11/04; A61M 15/00; A61M 15/06; A24F 40/10; A24F 40/20; A24F 40/48; A24F 40/42; A24F 40/46
See application file for complete search history.

(56) References Cited

U.S. PATENT DOCUMENTS 5,268,553 A    12/1993  Shimoji
5,934,289 A *   8/1999  Watkins ................. A24F 40/53
                                           131/328
(Continued)

FOREIGN PATENT DOCUMENTS

CN    201 088 138 Y    7/2008
CN    203 563 690 U    4/2014
(Continued)

OTHER PUBLICATIONS

Dan, "Blue diode laser 1W 445nm," Website Nov. 15, 2011 [online].
(Continued)

*Primary Examiner* — Samchuan C Yao
*Assistant Examiner* — Nathan M Le
(74) *Attorney, Agent, or Firm* — Perkins Coie LLP

(57) ABSTRACT

The present disclosure is a handheld apparatus that vaporizes plant-based or synthetic compounds, for the purpose of inhalation, or diffusion into an external environment. More specifically, the disclosure describes a handheld apparatus wherein a laser beam from an internal laser unit heats compounds, such as dried plant, tinctures, resins, or essential oils, to the compound's vaporization temperature for inhalation, or diffusion as part of aromatherapy or other holistic therapeutic treatments.

16 Claims, 11 Drawing Sheets

Related U.S. Application Data

(60) Provisional application No. 62/120,807, filed on Feb. 25, 2015.

(51) Int. Cl.

| | | |
|---|---|---|
| *A24F 40/42* | (2020.01) | |
| *A24F 40/46* | (2020.01) | |
| *A61M 15/00* | (2006.01) | |
| *A24F 40/10* | (2020.01) | |
| *A24F 40/20* | (2020.01) | |
| *A24F 40/48* | (2020.01) | |
| *A24F 40/40* | (2020.01) | |
| *A24F 40/50* | (2020.01) | |
| *A24F 40/485* | (2020.01) | |

(52) U.S. Cl.
CPC ............ *A24F 40/50* (2020.01); *A61M 15/06* (2013.01); *A24F 40/10* (2020.01); *A24F 40/20* (2020.01); *A24F 40/48* (2020.01); *A24F 40/485* (2020.01); *A61M 15/0021* (2014.02); *A61M 15/0023* (2014.02); *A61M 2205/368* (2013.01); *A61M 2205/8206* (2013.01)

(56) References Cited

U.S. PATENT DOCUMENTS

| | | |
|---|---|---|
| 6,053,176 A | 4/2000 | Adams et al. |
| 6,095,153 A | 8/2000 | Kessler et al. |
| 8,915,254 B2 | 12/2014 | Monsees et al. |
| 2002/0031917 A1 | 3/2002 | Nire et al. |
| 2004/0234914 A1 | 11/2004 | Hale et al. |
| 2004/0261475 A1 | 12/2004 | Artsiely |
| 2005/0117895 A1 | 6/2005 | Balch et al. |
| 2008/0118760 A1 | 5/2008 | Kaiser et al. |
| 2008/0156831 A1 | 7/2008 | Nakayama et al. |
| 2008/0257367 A1* | 10/2008 | Paterno .................. A24F 40/50 131/328 |
| 2010/0238547 A1 | 9/2010 | Choi et al. |
| 2012/0004865 A1 | 1/2012 | Porro et al. |
| 2013/0037041 A1 | 2/2013 | Worm et al. |
| 2013/0118498 A1 | 5/2013 | Robitaille et al. |
| 2013/0220315 A1 | 8/2013 | Conley et al. |
| 2014/0034071 A1 | 2/2014 | Levitz et al. |
| 2014/0053832 A1 | 2/2014 | Postma |
| 2014/0069424 A1 | 3/2014 | Poston et al. |
| 2014/0100455 A1 | 4/2014 | Goldman et al. |
| 2014/0158129 A1 | 6/2014 | Pratt, Jr. et al. |
| 2016/0021930 A1* | 1/2016 | Minskolf ................ A24F 40/51 131/329 |
| 2017/0020190 A1* | 1/2017 | Chang .................. H05B 3/0033 |
| 2017/0020193 A1* | 1/2017 | Davis .................. A61M 11/041 |
| 2017/0127722 A1* | 5/2017 | Davis .................... H05B 6/108 |

FOREIGN PATENT DOCUMENTS

| | | |
|---|---|---|
| WO | WO 98/17130 A1 | 4/1998 |
| WO | WO 2014/110119 A1 | 7/2014 |

OTHER PUBLICATIONS

Li C. et al. "Evaporation/Boiling on Thin Capillary Wick (I): Thickness Effects", 2006, Journal of Heat Transfer, vol. 128, p. 1312-1319.

International Search Report and Written Opinion dated Dec. 28, 2016, for International Application No. PCT/IB2016/001166, 9 pages.

Extended European Search Report dated Oct. 26, 2018, for European Application No. EP 16789369.2, 7 pages.

* cited by examiner

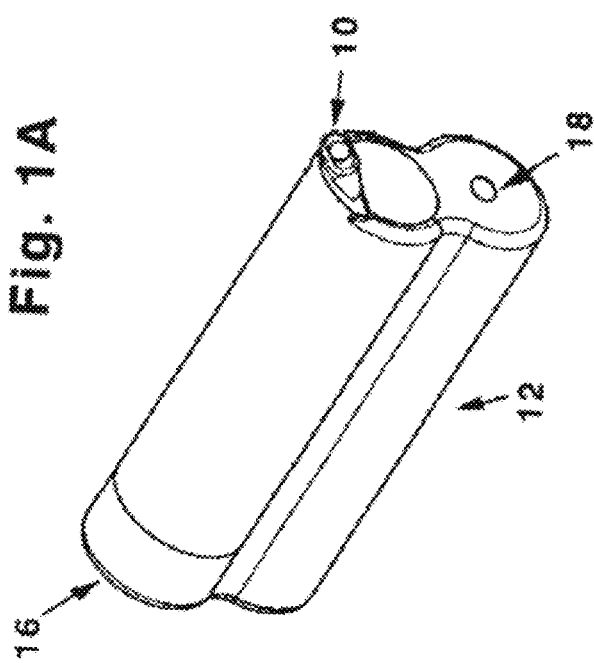

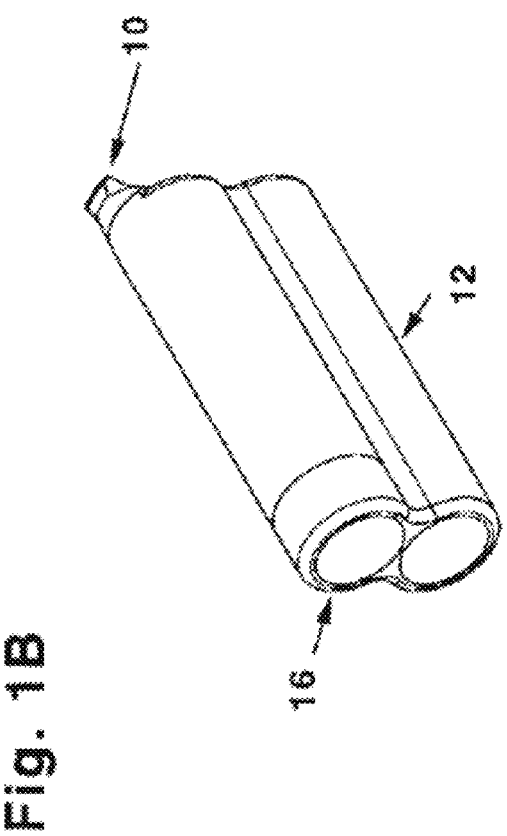

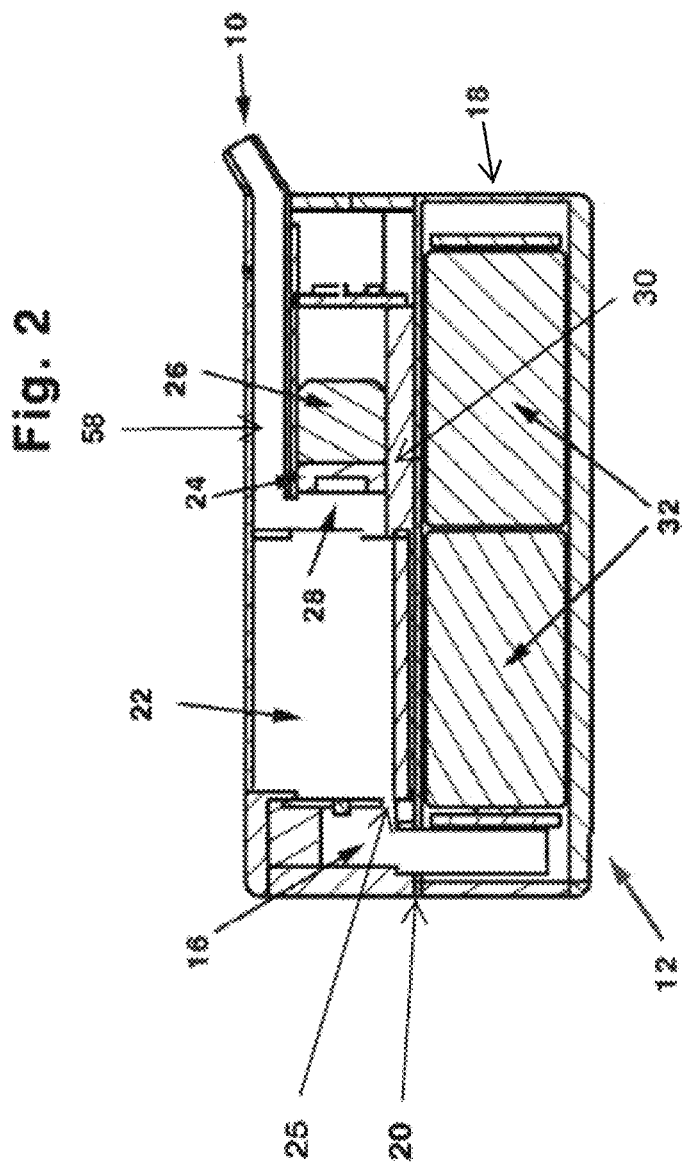

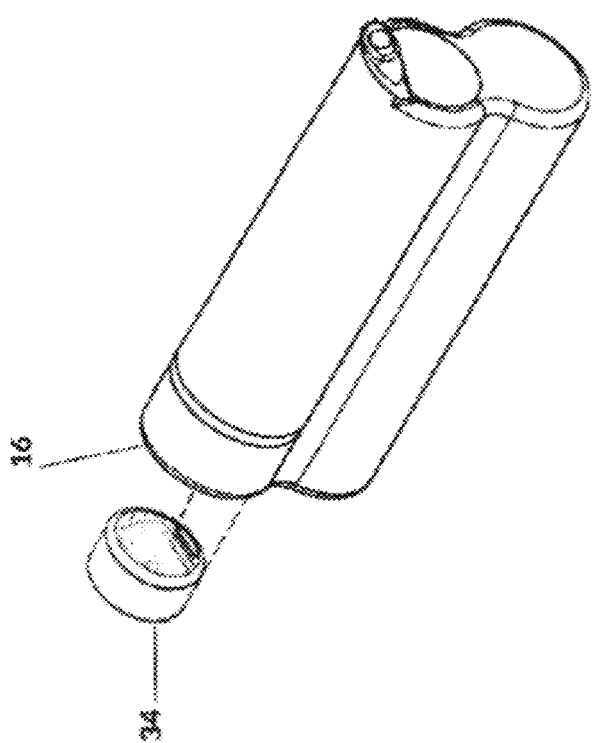

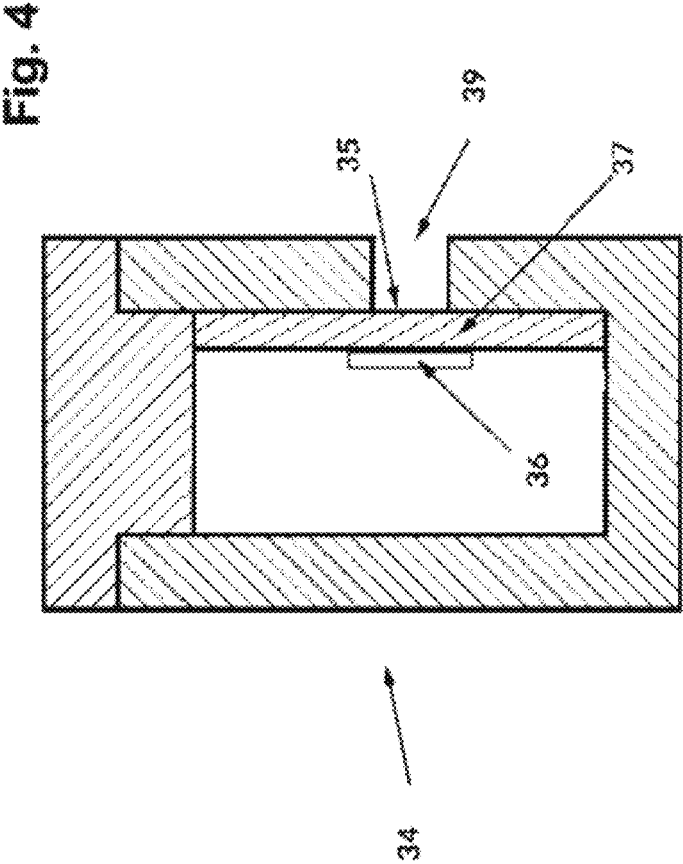

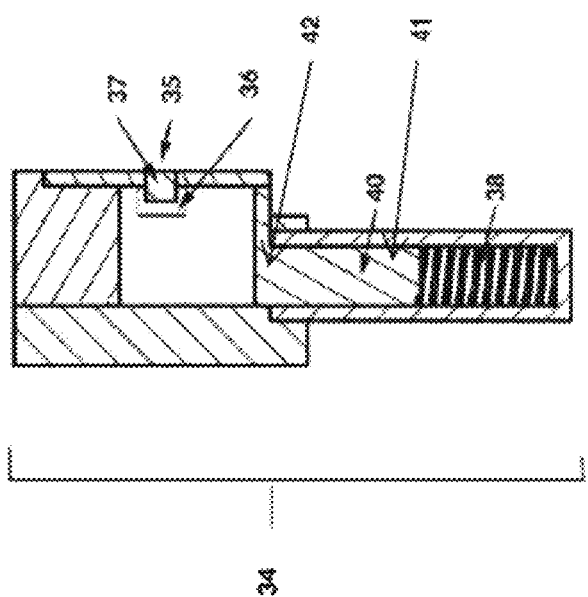

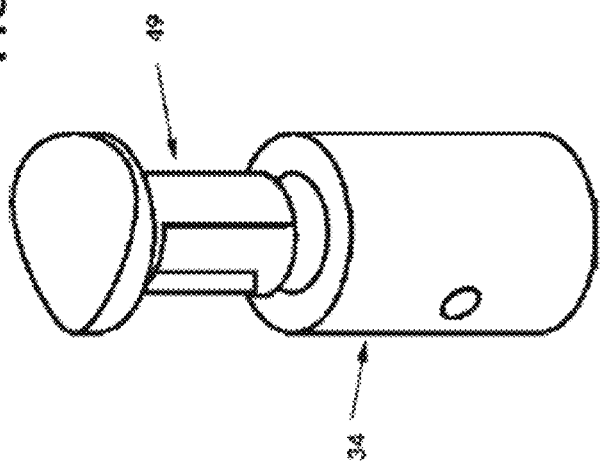

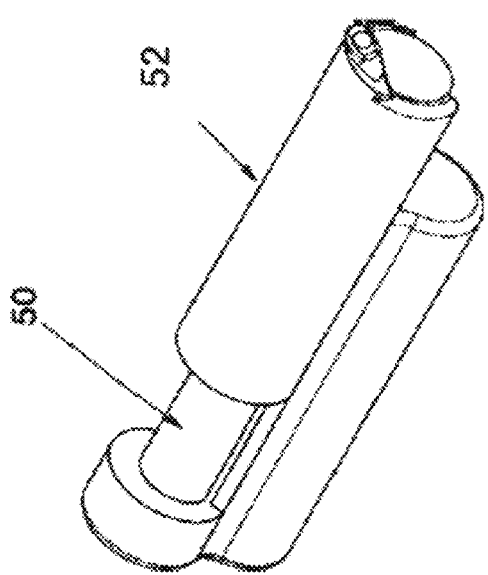

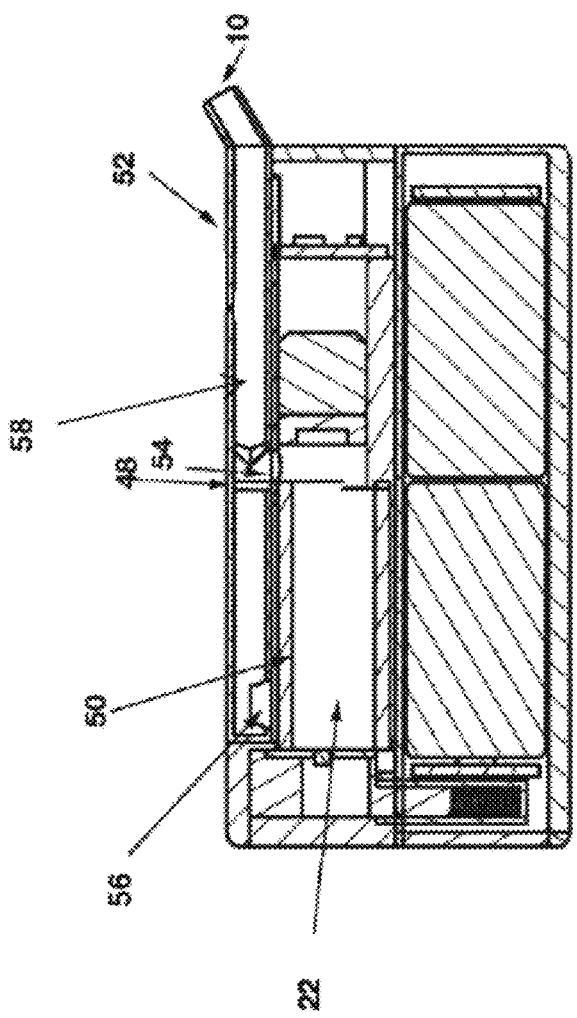

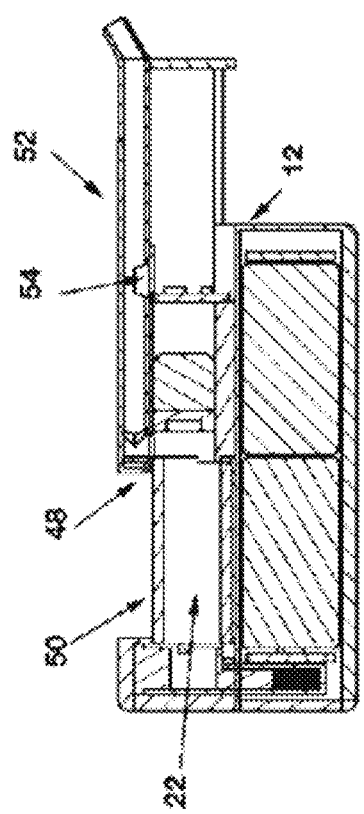

HANDHELD APPARATUS FOR VAPORIZATION OF PLANT-BASED OR SYNTHETIC COMPOUNDS BY LASER

CROSS-REFERENCE TO RELATED APPLICATIONS

This application is a Continuation of U.S. patent application Ser. No. 15/553,980, filed Aug. 25, 2017 and titled "HANDHELD APPARATUS FOR VAPORIZATION OF PLANT-BASED OR SYNTHETIC COMPOUNDS BY LASER," which is a U.S. National Stage Entry under 35 U.S.C. 371 of International Application No. PCT/IB2016/001166, filed Feb. 24, 2016 and titled "HANDHELD APPARATUS FOR VAPORIZATION OF PLANT-BASED OR SYNTHETIC COMPOUNDS BY LASER," which claims priority to and benefit of U.S. Provisional Application No. 62/120,807, filed Feb. 25, 2015, the entire contents of each of which are incorporated herein by reference in their entireties.

FIELD OF THE INVENTION

The present disclosure is a handheld apparatus that vaporizes plant-based or synthetic compounds, for the purpose of inhalation, or diffusion into an external environment. More specifically, the disclosure describes a handheld apparatus wherein a laser beam from an internal laser unit heats compounds, such as dried plant, tinctures, resins, or essential oils, to the compound's vaporization temperature for inhalation, or diffused as part of aromatherapy or other holistic therapeutic treatments.

BACKGROUND OF THE INVENTION

The therapeutic use of plant-derived compounds, synthetics analogues, or plant extracts are gaining new attention as alternative treatments for infections, stress, and other health problems as well as promoting physical and psychological well-being.

It has been suggested that breathing in fragrant air stimulates the odor-sensing nerves in the nose sending impulses to the limbic system of the brain or activating hormones or enzymes in the blood that stimulate the adrenal glands.

More than 100 plants are thought to have beneficial effects when used as either whole leaf or as oils or resins. Common plants include flowers (rose, *narcissus*), roots (orris), leaves and needles (*eucalyptus*, pine), resins (turpentine), seeds (caraway), fruits (lemon, lime), berries (cloves), bark (cinnamon) and wood (cedar), spices (basil, anise, nutmeg, cumin, oregano), substances related to plant-based or synthetic medicine (marijuana, tobacco, St. John's wort).

When heated to certain temperatures, these compounds are converted into gaseous form, producing a micro-fine mist containing the beneficial molecules, which can then be inhaled, either directly as a concentrated dose or in a diffused form by expelling the gaseous vapor into the air of the surrounding environment.

Those preferring a concentrated dose will often smoke the compounds, as is seen with cigarettes or marijuana.

However, smoking these compounds subjects them to extremely high temperatures, causing a combustion reaction, creating toxic byproducts that can lead to a multiple of diseases such as lung cancer, asthma and chronic bronchitis.

Combustion is an exothermic reaction causing the compounds to undergo oxidation.

In some cases, the temperatures are high enough to cause a pyrolysis reaction, wherein the compounds undergo a thermochemical decomposition, breaking the chemical bonds between carbon atoms, releasing large amounts of volatile and semi-volatile smoke constituents.[1] ≠[1] Norman, A. (1999). Smoke Chemistry. In: D. Layten Davis & Mark T. Nielsen. Eds. Tobacco Production, Chemistry and Technology, Oxford; Blackweil Science Ltd.

A major group of compounds formed during pyrolysis is that of the polynuclear aromatic hydrocarbons. Ethylene glycol is pyrolytically converted to the human carcinogen ethylene oxide.[2] ≠[2] IARC (1994a) Ethylene oxide. In: Some industrial chemicals. Lyon, International Agency for Research on Cancer, pp 73-159 (IARC Monographs on the Evaluation of Carcinogenic Risks to Humans, Volume 60).

According to the National Institute of Health, studies suggest that "the chemical constituents in tobacco smoke that present health concerns increased as the temperature increased from 300° C. to 1,000° C., but some compounds (e.g., acrolein and formaldehyde) reached their maximum yield at 500° C. and the yield remained approximately the same at higher temperatures.[3] ≠[3] Centers for Disease Control and Prevention (US); National Center for Chronic Disease Prevention and Health Promotion (US); Office on Smoking and Health (US). Atlanta (Ga.): Centers for Disease Control and Prevention (US); 2010.

For example, the temperature of cigarette coal can range from a resting (smoldering) temperature of around 600° C. to peak puff temperatures exceeding 900° C. during a 35 mL, 2-sec puff (the pyrolysis/distillation zone).

More than 5,000 smoke constituents have been identified in cigarette smoke, with about 150 identified as smoke toxicants.[4] ≠[4] Rodgman, A., Perfetti, T. A. (2008). The chemical components of tobacco and tobacco smoke. USA: Taylor and Francis Ltd.

However, it is well known in the industry that heating plant materials or other synthetic medicinal products at lower temperatures, a technique known as vaporization, releases beneficial organic compounds.

Plant products, for example, vaporize at much lower temperatures than are seen during combustion or pyrolytic reaction, as shown in in the list below.

Chamomile—Vaporization temperature: 374° F./190° C.
Passion Flower—Vaporization temperature: 309° F./154° C.
Green Tea—Vaporization temperature: 374° F./190° C.
Peppermint—Vaporization temperature: 331° F./166° C.
*Eucalyptus*—Vaporization temperature: 266° F./130° C.
St. John's Wort—Vaporization temperature: 302° F./150° C.
*Cannabis*—Vaporization temperature: 356-410° F./180-210° C.
Tobacco—Vaporization temperature: 257-302° F./125-150° C.

As shown, some temperatures are displayed in ranges due to multiple constituents within the plant compounds, each having unique vaporization temperatures.

However, while vaporization profiles are equivalent for constituents across various forms, combustion points may vary.

For example, cannabinoid concentrates, such as resins or waxes, are very lipid soluble, but water insoluble, resulting a very viscous substance. Cannabinoid concentrates resemble a thick, sticky, gummy resin and are less likely to combust than the dry flower or leaf forms.

Additionally, concentrates are typically more potent than non-concentrates.

THC concentrations for *cannabis* resin is typically 5-10%, rarely exceeding 12% whereas dry *cannabis* normally contains 3-4% THC. The THC content of hash oil is much more variable with levels ranging from 15% to over 60%.[5] ≠[5] L. A. King, Drug content of powders and other illicit preparations in the UK. Forensic Science International 85 p. 144 (1997) 135-147.

However, it is the safety profile of vaporization over combustion methods that have made vaporization of organic and synthetic compounds for inhalation so popular.

A recent study on the vaporization of *cannabis* stated that its major finding was a drastic quantitative reduction in non-cannabinoid compounds in the vapor strongly suggesting that vaporization is an effective method for delivering medically active cannabinoids while effectively suppressing other potentially deleterious compounds that are a byproduct of combustion.[6] ≠[6] Gieringer D., Laurent S. J., Goodrich S. *Cannabis* Vaporizer Combines Efficient Delivery of THC with Effective Suppression of Pyrolytic Compounds. Journal of *Cannabis* Therapeutics. 4:7-27.

This view was expressed by the Institute of Medicine in its report on medical marijuana (IOM 1999, Executive Summary p. 8): "Because of the health risks associated with smoking, smoked marijuana should generally not be recommended for long-term use. . . . The goal of clinical trials of smoked marijuana would not be to develop marijuana as a licensed drug, but rather as a first step towards the possible development of non-smoked, rapid-onset delivery systems." [7] ≠[7] Id.

The safety profile of vaporization has thus paved the way for a host of vaporizing apparatuses, the most popular being e-cigarettes.

The majority of e-cigarette apparatus' resemble traditional cigarettes, but instead of tobacco, the e-cigarette uses a cartridge filled with a nicotine infused liquid, which is heated by a battery powered coil.

The resulting vapor is released into a chamber where it can be inhaled, much like a traditional cigarette.

The aerosol produced has a simpler more predictable composition and maintains the general smoking experience.

However, the heating element in an e-cigarette does not produce temperatures required to vaporize many plant-based or synthetic materials.

For example, marijuana vaporization requires a temperature range between 180-210° C. to release the beneficial Cannabinoids and Terpenes within the plant.

*Cannabis* contains sixty-six cannabinoids, the most well known being delta-9-tetrahydrocannabinol (Δ9-THC), which is the main psychoactive ingredient in *cannabis*.

As well, *Cannabis* has over 120 terpenes responsible for producing various fragrances, such as floral, citrus, woodsy, and plant-based or synthetic.

Cannabinoids are highly combustible and many of the delicate terpenes responsible for the fragrances are easily destroyed in a combustion reaction.

With vaporization, more than twice as many cannabinoids and terpenes are delivered to the user than one would get from smoking.

Gas chromatograph mass spectrometer (GCMS) examining the gas components resulting from vaporization showed that the vapor was remarkably clean, consisting 95% of THC, the principal psychoactive constituent of *cannabis*, with the remaining 5% consisting of terpenes and other cannabinoid related substances.

In contrast, over 111 different components appeared in the gas of the combusted smoke, with non-cannabinoids accounting for as much as 88% of the total gas content of the smoke.[8] ≠[8] Norman, A. (1999). Smoke Chemistry.

Examples of vaporizers on the market today are the Pinnacle Pro Vaporizer by VaporBlunt and the Volcano Digit, by Storz and Bickel, which both use a coil type heating element.

The Pinnacle Pro is a handheld vaporizer that looks similar to an e-cigarette. The unit is approximately five inches long, an inch in diameter and weighs about 100 grams. The vaporization material is placed at one end of the pipe, along with cartridges for flower or hash oil.

The unit heats the vaporization material by activating the heating element, which heats a conductive substance that is in direct contact with the vaporization material. The heating element is only one inch from the mouthpiece, which can make the vapor hot enough to irritate or burn the throat, depending upon which material is being vaporized; a common safety concern of current portable vaporizers. To compensate, the unit can be used in conjunction with a water pipe, which can reduce the heat of the vapor. Another downside of current Vaporizer technology is the start-up time.

The Pinnacle Pro takes almost one minute to heat up before a user can inhale the vapor. Also, its significant power requirements allow for only about an hour of usage before the unit needs to be recharged. The power and heat generation needs often lead to a shortened shelf life.

One of the most popular Vaporizers is the Volcano Digit, which is a cone shaped tabletop unit measuring approximately 7.9 inches at it base and 7.21 inches high, weighing 4.0 pounds. The Volcano uses a conduction method, albeit a larger one.

The advantage of the larger units is a larger conduction plate, plate temperature accuracy, and a larger chamber to hold the vaporization material.

However, they are not portable, and the process is relatively complex and time consuming verse that of e-cigarettes. For the Volcano, a user adds the vaporizable contents into the heating chamber.

The Volcano unit is turned on and a temperature chosen via a digital readout. It takes approximately four minutes to reach vaporization temperature. The user must then attach a vapor balloon to the top of the heating chamber.

Over the course of about 30 seconds, a plastic balloon connected to the device fills up with vapor. The user attaches a mouthpiece to the balloon from which the vapor inside can be inhaled.

While current Vaporizers may function satisfactorily under certain circumstances, there is a need for an improved portable Vaporizer that can be used to smoke plant based materials, with short startup times, low power consumption, long battery life, flexible temperature control, and enhanced safety, without the risk of metal "off gassing" of toxic vapors.

BRIEF SUMMARY OF THE INVENTION

The present disclosure is a handheld apparatus that vaporizes plant-based or synthetic compounds, for the purpose of inhalation, or diffused into an external environment.

The current embodiment consists of, but is not limited to, an apparatus wherein a laser diode unit is enclosed in a heat-diffusing housing, the laser being focused through a single-element lens toward a reaction chamber containing vaporization material.

In a preferred embodiment, the housing is made of aluminum with a Viewport Cover that slides toward the mouthpiece into an open position, revealing the reaction chamber, viewable through a light spectrum specific, safety plastic or glass view-port balanced to block dangerous light radiation emissions, but transparent enough to safely see the reaction in the cartridge.

The vaporization compounds can be loaded directly into the reaction chamber, or into a reaction cartridge, which can then be placed into the reaction chamber.

The reaction cartridge can be constructed of a multiple of materials, depending upon the type and composition of the vaporization compounds.

For example, a reaction cartridge filled with non-concentrate compounds, such as leaf or flower, could be made of glass or other transparent material wherein the laser could directly heat the non-concentrate.

Alternatively, the reaction cartridge could be made of a thermally conductive substrate such as ceramic, that can convert the energy from a laser beam into heat.

The laser unit, or a multiple of laser units, produces a low wavelength laser beam, which is focused through a lens onto the exterior of the reaction cartridge, wherein the laser energy is converted into heat, raising the temperature along the heat envelope within the reaction cartridge.

The heat envelope is the area adjacent to or in contact with the substrate in which is equal to or greater than the vaporization point of the vaporization material residing in the reaction cartridge.

The amount of vapor released is dependent upon several factors including, but not limited to, the thermal conductivity and size of the substrate, volume of substrate, and the length of time the laser is engaged.

In a preferred embodiment, the reaction cartridge includes an air vent and a vapor escapement.

The air vent allows air from the external environment to enter the reaction cartridge or allow vapor from with the cartridge to be diffused into the surrounding environment.

The vapor escapement allows vapor to leave the reaction chamber and enter a vapor chamber, without debris, such as unvaporized material that may remain in the reaction cartridge.

A vapor tube connects a mouthpiece to the vapor chamber.

Inhaling forces air in through the air vent and into the reaction cartridge. Vapor residing within the reaction cartridge is then moved into the vapor chamber, then out through the vapor tube and mouthpiece.

Conversely, blowing into the mouthpiece forces air through the vapor tube, into the vapor chamber and into the reaction cartridge where the vapor residing in the cartridge is expelled through the air vent into the surrounding environment.

In one embodiment, the user determines the amount of vapor available for inhalation or diffusion by choosing the duration or power intensity of the laser.

A recommended approach includes a power switch that engages the laser only through an active engagement by a user, such as holding down a button or touching a captive switch. When not engaged, the laser remains in the "off" position. This approach will ensure that the laser is not inadvertently engaged for unattended long periods, improving both safety and potentially increasing the useable life of the laser unit.

To enhance the heat dispersion, the laser heat sink is attached to the vaporization unit's main housing, which consists of a solid, heat diffusing material, such as aluminum. The excess heat generated by the laser is absorbed by the heat sink, and then excess heat is transferred and dispersed throughout the housing.

The laser can be powered in a number of ways. The preferred embodiment uses rechargeable lithium ion batteries, although any power system, including standard removable batteries or a wall plug are contemplated.

In the present embodiment, the batteries are situated below the laser chamber, which allows the unit to maintain a compact profile and a separate inhalation conduit preventing the inhalation of battery fumes, however, the battery location is variable.

The vaporization unit can be used to vaporize both concentrates and non-concentrates.

However, as concentrate potency is much higher in concentrates than non-concentrates, less concentrate will need to be vaporized than non-concentrates to achieve the equivalent inhalation or diffusion of active constituents, such as THC or terpenes.

In one embodiment wherein the reaction cartridge contains only concentrates, the laser unit focuses a Gaussian laser beam on a thermally conductive substrate, within a portion of the reaction cartridge, wherein the concentrate material is within the substrate's heat envelope, in which the temperature is above the vaporization point for the compounds within the reaction chamber.

In a preferred embodiment, the substrate is blackbody material with a high emissivity rating. Emissivity (e) is the characteristic parameter for the absorption and emission of thermal radiation of a surface.

In a preferred embodiment, the blackbody substrate is micro-porous wherein a portion of the blackbody substrate outside of the heat envelope acts as a wick, drawing a portion of liquid concentrate through the micro-porous structure by capillary action.

In an additional embodiment, a spring and plunger within the reaction cartridge pushes sticky concentrate material, such as waxes or resins, toward the blackbody substrate's heat envelope.

Another embodiment includes a sliding housing cover that exposes a transparent viewport wherein the user can view the vaporization reaction as well as see the amount of vapor available for inhalation or diffusion.

In embodiments wherein the vaporization material is loaded directly onto the reaction chamber or wherein the reaction cartridge is made of a transparent material, the viewport will also allow the user to see the amount of vapor material remaining.

To operate the unit, the user removes the reaction cartridge, filling it with the vaporization materials and places the reaction cartridge back into the reaction chamber by sliding it through a side port. Pre-filled cartridges are contemplated.

The user can choose a temperature by adjusting the power regulator. The invention contemplates pre-programmed positions that correspond to different plant-based or synthetic vaporization temperatures.

The user breathes in through the mouthpiece to allow air into the chamber, which exits through the vapor hole into the vapor tube and out the mouthpiece. For aromatherapy, the reverse process is engaged.

Other objects and advantages of this invention will become apparent from the following description taken in conjunction with any accompanying drawings wherein are set forth, by way of illustration and example, certain embodiments of this invention. Any drawings contained herein constitute a part of this specification and include exemplary embodiments of the present invention and illustrate various objects and features thereof.

BRIEF DESCRIPTION OF THE DRAWINGS

FIGS. 1A and 1B show an external view of the Vaporizer Unit.

FIG. 2 shows a cross-section of the Vaporizer.

FIG. 3 shows an embodiment wherein the Reaction Cartridge is placed into Reaction Chamber.

FIG. 4 shows a left side cutaway of the Reaction Cartridge [34] with a wick system designed for concentrates.

FIG. 5 shows a Spring and Plunger mechanism for moving concentrate toward the heat envelope.

FIG. 6A and FIG. 6B shows an additional embodiment that uses a Reaction Cartridge Insert to load low viscosity concentrates into the Reaction Cartridge.

FIG. 7 shows left side view of the Vaporizer wherein a sliding cover reveals a Viewport.

FIG. 8 shows a cutaway view of the Vaporizer in the closed position.

FIG. 9 shows a cutaway view of the Vaporizer in the closed position.

DETAILED DESCRIPTION OF THE DRAWINGS

Figure 6A:
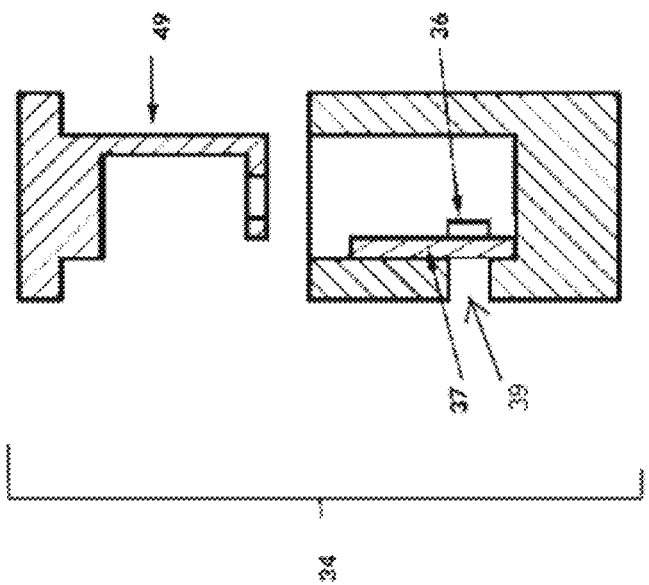

The present disclosure is a handheld apparatus, which uses a laser to vaporize plant material for the purpose of vapor inhalation. More specifically, the disclosure describes a self-contained unit that safely focuses the energy generated by a laser to vaporize plant-based or synthetic materials, such as dried plant, tinctures, resins, or essential oils, for inhalation or as part of aromatherapy or other holistic therapeutic treatments.

The current embodiment consists of, but is not limited to, a mobile apparatus wherein a laser diode is enclosed in a heat-diffusing housing, the laser being focused through a single-element lens toward a reaction cartridge containing plant-based or synthetic material, the planet based material being vaporized by the laser, the vapor then being inhaled by the user or expelled into the surrounding area for aromatherapy.

The Vaporizing Unit is designed to be compact, so that users can easily fit it in a pocket.

FIGS. 1A and 1B show an external view of the Vaporizer Unit. FIG. 1A is an upper left side rear view of the Vaporizer upper left side, viewed from rear of the Vaporizer and FIG. 1B shows an upper left side rear view of the Vaporizer.

The Vaporizer of the preferred embodiment is designed as an extruded "FIG. 8" which is ergonomic and comfortable to hold. However, the Vaporizer can be designed in a number of configurations, including, but not limited to, a traditional "pipe" configuration.

On the rear end of the Vaporizer is a mouthpiece [10] from which the user will inhale the vapor, or blow into for the aromatherapy function.

The Mouthpiece [10] is attached to the Main Housing Unit [12], which encloses the functional components.

On the front end of the Main Housing Unit [12] is the Reaction Chamber [16], which holds the plant-based or synthetic materials that will be vaporized.

Below the Mouthpiece [10], located on the front of the Main Housing Unit [12] is the Power Switch [18].

FIG. 2. shows a cross-section of the Vaporizer, as viewed from the left side of the unit. The internal components are as follows:

At the rear of the unit is the Mouthpiece [10].

A Vapor Tube [20] connect the Mouthpiece [10] to the Vapor Chamber [22], which hold the vapor until inhaled or expelled by the user.

In the current embodiment, the Main Housing Unit [12] is a single molded aluminum unit in which the Vapor Tube [20] and the Vapor Chamber [22] are integrated into the Main Housing Unit [12] as part of the mold, however, other methods are contemplated, such as separate plastic or metal tubing.

A Laser Diode [24] is attached to a Heat Sink [26] with the laser beam, directed through a Focusing Lens [28] toward a Reaction Chamber [16], which contains the plant-based or synthetic vaporization materials, including concentrates, such as oils and resins and/or non-concentrates, such as leaf material.

Engaging the laser heats the plant based materials in the Reaction Chamber [16] to the vaporization point. The resulting vapor collects within an open area of the Main Housing Unit, described here as a Vapor Chamber [22], until the user inhales or expels the vapor.

When a user inhales, air from the external environment is forced through an Air Vent [20], and into the Reaction Chamber [16], through a Vapor Escapement [25] into the Vapor Chamber [22], and out through the Vapor Tube [58] and Mouthpiece [10]

The Air Vent [20] and Vapor Escapement [25] act as screens, allowing air and vapor to leave the reaction chamber without any vaporization materials.

Various configurations are contemplated including metal screens.

In the current embodiment, the Vapor Chamber [22], Vapor Tube [58], Air Vent [20] and Vapor Escapement [25] are constructed as part of the mold of the Main Housing Unit [12], but the invention contemplates other approaches wherein the components are separate and distinct connected to, rather than part of, the interior of the main housing.

When diffusing, the opposite occurs wherein air is pushed from the Vapor Tube [58] and into the Vapor Chamber [22], through the Vapor Escapement [25], into the Reaction Chamber [16] where the vapor is expelled through the Air Vent [20] into the external environment.

Although any type of directed high intensity light is contemplated, the preferred embodiment uses a blue, low wavelength laser, such as is found in the M140 laser diode, which contains a blue 445 nanometer (nm) laser.

A single low wavelength lasers provide an excellent balance between performance, portability and power consumption, however, higher-powered lasers or version containing multiple lasers are contemplated. For safety considerations, the preferred configuration has the laser pointing away from the user, but other laser positions are contemplated.

The Laser Diode [24] is attached to the Heat Sink [26], which is a standard component of most "off the shelf" lasers, including the M140. The heat generated in the Laser Diode [24] can be dispersed by the Heat Sink [26] which is made from an efficient thermally conductive material, such as copper or brass.

The longer the laser is fired, the more material is vaporized and thus, the more vapor is available for inhalation. However, prolonged firing of the laser could build up excess heat that the can overwhelm an "off the shelf" Heat Sink [26], damaging the Laser Diode [24] or resulting in injury to the user.

To avoid excess heat buildup, laser-based products often utilize automatic shutoff controls for the Laser Diode [24], which limits the time the laser can be engaged, and then require a cooling down period before their laser can be reactivated.

However, a more effective approach is to extend the Heat Sink's [26] thermal conductivity by attaching it to additional thermally conductive materials.

In a preferred embodiment of the current invention, the Main Housing Unit [12] is constructed from a thermally conductive the material, wherein the Heat Sink [26] is attached directly to the Main Housing Unit [12], allowing excess heat from the Heat Sink [26] to transfer from the Heat Sink [26] to the Main Housing Unit [12]. The large conductive area of the Main Housing Unit [12] allows it to remain cool to the touch.

The preferred material for Main Housing Unit [12] construction is aluminum, however, any material with high thermal conductivity is contemplated.

The current embodiment uses aluminum which has a thermal conductivity rating of 0.50 (cal/sec)/($cm^2$ C/cm) or 205 (W/m K).[9] ≠[9] Young, H. D., & Sears, F. W. (1992). University physics. Reading, Mass.: Addison-Wesley Pub. Co. Table 15-5.

Aluminum provides an excellent balance between weight, thermal conductivity, ease of construction, and cost.

A Laser Diode [24] requires a Focusing Lens [28] to direct the intensity of the laser beam. The tighter the beam, the higher the heat generated.

The current embodiment utilizes a single-element AR coated glass Focusing Lens [28], such as a G2 series lens, which is well known in the art to be more efficient at light transmission than traditional 3-element lenses, however, other lens types are contemplated.

Power requirements for the laser is dependent upon the Laser Diode [24] being used. The current embodiment uses a constant current Diode Driver Circuit that can generate up to 2 watts.

In the current embodiment, the Laser Diode [24] is powered by two standard rechargeable 18350 3.7 v protected Li-Ion Batteries [32].

The configuration in FIG. 2 shows the Batteries [32] located in the lower part of the Main Housing Unit [12], below the Laser Diode [24].

The advantage of this configuration is that the vapor tube is located away from the batteries, minimizes the potential for inhalation of toxic vapors emitted by the batteries.

However, the battery location is variable. Custom battery profiles, such as flat batteries or other locations, including but not limited to, placing the Batteries [32] between the Laser Diode [24] and the Mouthpiece [10] (as shown in the referenced Provisional Patent #62120807) are also contemplated.

To operate the unit, the user holds the Power Switch, [18] which engages the Laser Diode [24].

The user chooses the duration that the Laser Diode [24] is engaged and the power curve at which the diode will operate, vaporizing as much of the material in the Reaction Chamber [16] as the user wishes to inhale.

For safety reasons, it is recommended that the Power Switch [18] engage through a continuous action, such as holding down a button, so that the laser will shut off when the action complete.

One embodiment uses a touch capacitive Power Switch [18].

In a preferred embodiment, a power regulator is included, which enables the user to change the laser power curve, increasing or decreasing the heat from the laser to the proper vaporization temperatures for varying types of vaporization materials.

An example of a power regulator is Blitzbuck V5 adjustable diode driver, which has a fluctuating output.

The heat of the laser beam will be controlled by adjusting the output amps, which is adjusted through an adjustment screw in the Bitzbuck V5.

Alternatively, a relay switch can be used to change between multiple settings, each setting being equivalent to the vaporization temperature required for a multiple of plant-based or synthetic materials.

The invention contemplates a pre-programmed regulator that delivers power that corresponds to different plant-based or synthetic vaporization points.

The laser may also be adjusted to allow for a wide dispersal or a focused beam.

FIG. 3 shows an embodiment wherein the Reaction Cartridge [34] is placed into Reaction Chamber [16] through an open area on the back of the Vaporizer.

Using a Reaction Cartridge has several advantages over loading vaporization materials directly into the Reaction Chamber [16], including ease of cleaning the unit as well as being able to pre-load multiple Reaction Cartridges [34] or being able to produce pre-filled disposable Reaction Cartridges [34].

In another embodiment, as an added safety feature, removal of the reaction cartridge breaks a circuit, disabling the laser diode from firing.

Using a Reaction Cartridge [34] has an added advantage of being able to vary the materials used to construct the Reaction Cartridge [34] based up on the chemical profile of the vaporization material.

For example, a cartridge filled with loose leaf materials may benefit from a Reaction Cartridge [34] constructed of a thermally conductive material wherein the entire Reaction Cartridge [34] is heated by the laser, as opposed to vaporizing the leaf material directly.

In one embodiment, the Reaction Cartridge is constructed from a material with high thermal conductivity and heat transfer, also known as a substrate.

Conductive heat transfer can be expressed with "Fourier's Law":

$$q = kA\frac{dT}{dx},$$

where q=the heat flow rate by conduction (W·$m^{-2}$), k=the thermal conductivity of body material (W·$m^{-1}$·$K^{-1}$), 'A=the cross-sectional area normal to direction of heat flow ($m^2$) and $$\frac{dT}{dx} = \text{the temperature gradient } (K \cdot m^{-1}).$$

An example of a reaction cartridge substrate for vaporization of non-concentrate (flower or leaf) material is Heatron's Ceramic Core Aluminum Nitride has excellent thermal conductivity and uniformity, effective to temperature of up to 1,000° C., with a Maximum Watt Density of 1,000 W/in, a thermal conductivity measure of 220 W/mK and a Ramp-Up Rate of 500° C./sec.

Vaporizing concentrates, on the other hand, require less material to be vaporized than non-concentrates, wherein a tighter laser beam heating a smaller substrate is more efficient.

The dimensions of the substrate for concentrates are variable, dependent on a multiple of factors including the size and shape of the Reaction Cartridge [34], the desired vaporization temperature, the types of concentrate and the desired amount of vapor produced.

Additionally, some concentrates have properties that may affect the even distribution of vaporization within the Reaction Cartridge [34].

For example, a concentrate of sticky resin may adhere to the interior surface of the Reaction Cartridge [34], away from the substrate.

Additionally, some concentrates may undergo an intermediate state change prior to vaporization. For example, waxes characteristically exhibit a relative low melting point between 113-160° F. depending upon the chemical composition of the wax, wherein some of the FIG. 4 shows a left side cutaway of the Reaction Cartridge [34] with a wick system designed for concentrates.

While the invention contemplates a Reaction Cartridge [34] containing concentrate for a single inhalation, the preferred approach is to fill the Reaction Cartridge [34] with a concentrate for multiple uses.

In the embodiment show here, the Reaction Cartridge [34] is constructed of a transparent material, wherein the user can view the amount of concentrate within the cartridge, although a non-transparent Reaction Cartridge [34] is contemplated.

A thermally conductive substrate is located on a portion of the interior of the Reaction Cartridge [34], wherein it can be hit with the laser.

In a preferred embodiment, the substrate is Blackbody Substrate [37].

A black body (ideal heat emitter) would fully emit and absorb all electromagnetic radiation incident upon it with every wavelength (e=1). In contrast, the surface of a real body only emits part of this radiation. Thus, real objects are called "gray" bodies (e<1). The emissivity of a body thus describes the amount of radiation that it emits in comparison with a black body.

The purpose of the blackbody substrate is to absorb and distribute the maximum amount of radiant energy from the light and transform it into thermal energy for vaporization, which increases the energy efficiency of the vaporization process.

The distribution of power that a black body emits with varying frequency is described by Planck's law.

Planck's law for the energy EA radiated per unit volume by a cavity of a blackbody in the wavelength interval $\lambda$ to $\lambda+\Delta\lambda(\Delta\lambda$ denotes an increment of wavelength) can be written in terms of Planck's constant (h) the speed of light (c), the Boltzmann constant (k), and the absolute temperature $$E_\lambda = \frac{8\pi hc}{\lambda^5} \times \frac{1}{\exp\left(\frac{hc}{kT\lambda}\right)-1}$$

where The value of Planck's constant is found to be $6.62606957 \times 10^{-34}$ joule-second, with a standard uncertainty of $0.00000029 \times 10^{-34}$ joule-second.

The majority of the vaporizing materials have transparent and/or reflective optical characteristics that wastes the radiant energy by not absorbing it.

The blackbody substrate absorbs the incidental radiant energy that would normally be reflected or transmitted through the target material.

The closer the characteristics of the substrate are to an ideal blackbody, the more efficient it will be at absorbing the radiant energy from the light and converting it into thermal energy for vaporization.

Therefore, the higher the emissivity, the less power is required by the laser to transfer the thermal energy as heat into the substrate.

The Blackbody substrate efficiently absorbs energy from the laser and emits it as heat in a highly localized area.

The relationship governing the net radiation from hot objects is calculated using the Stefan-Boltzmann law:

$$P = e\sigma C(T^4 - T_C^4)$$

where P=net radiated power, A=the radiating area, $\sigma$=Stefan's constant $(5.6703 \times 10^{-8}$ watt/m2K$^4$), e=emissivity, T=the temperature of the radiator, and $T_c$=the temperature of the surroundings.

The substrate could also be colored the complimentary frequency of the light. For instance, the 445 nm blue light is readily absorbed by its complimentary colored pigment 580 nm yellow. The problem is discoloration, which makes black a more ideal candidate.

The blackbody substrate also regulates the volume of the material to be vaporized by a capillary action, which vaporizes a thin layer of vaporizing material adjacent to the substrate.

A thin layer is much more efficient as it reduces the required energy to reach the point of vaporization because there is less surrounding material to absorb the thermal energy.

Although many materials could be used as the blackbody substrate, the most ideal material is one that is highly refractory, porous, stable from oxidization, and optically absorbent.

The material must be able to remain inert and stable at the required vaporization temperatures between 200-800 degrees F.

The material must be porous enough to wick the vaporizing material from the main reservoir and transport it into the target dimple.

Certain materials, especially metallic materials, have a tendency to oxidize after repeated heating and cooling cycle. This oxidization has been known to off-gas fumes, and thus should be avoided.

It is possible to vaporize the material without using a blackbody substrate. This would require significantly more output power of the currently used diode.

It can also be achieved by increasing the optical density by adding a secondary focusing lens element.

First, the light beam is nominally collimated with a collimator lens. Then the collimated beam is focused to the required optical density using either a plano-convex or an aspherical lens. However, both solutions would require much more expensive lenses or diodes.

In the current embodiment, a tight Gaussian laser beam is directed at the Target Point [35], wherein the laser energy is converted to heat in the localized area of the target Point, heating the Blackbody Substrate [37] to a temperature at or above the vaporization temperature of the concentrate but below its combustion temperature.

In one embodiment a Laser Hole [39] (see, for example, FIG. 6A) on the exterior of the Reaction Cartridge allows the laser unimpeded access to the Blackbody Substrate [37]

The Blackbody Substrate [37] distributes the heat, vaporizing material within its Heat Envelope [36], which is the thin layer adjacent to the substrate.

Concentrates lying outside of the Heat Envelope [36] will not be vaporized.

The black body substrate exposed to the interior of the cartridge adjacent to the target area will emit heat, creating a localized heat envelope where the temperature is at or above the vaporization point of the concentrate but below the combustion point of the concentrate.

The localized heat envelope allows additional control over the amount of vapor a user desires than with a non-blackbody substrate.

In a preferred embodiment, the blackbody substrate is micro-porous wherein a portion of the blackbody substrate outside of the Heat Envelope [36] acts as a wick, drawing a portion of liquid concentrate through the micro-porous structure by capillary action.

As a result, the heat emitted by the Blackbody Substrate [37] is localized to the laser target area and not transferred evenly throughout the Blackbody Substrate [37], unlike other thermally conductive substrates such as ceramics or iron, with less emissivity.

This feature makes the Blackbody Substrate ideal for controlling the vapor output of dense and potent concentrates.

The present invention contemplates loading concentrate through an open portion of the Reaction Cartridge [34], which can be closed using a multiple of mechanisms including, but not limited to, a screw cap, or a door held in place by force exerted on a rubber grommet attached to the door's interior side.

In order for the Reaction Cartridge [34] to easily load into the Reaction Chamber [16], it is preferred that the mechanism for closing the Reaction Cartridge [34] be at the top or at the bottom of the cartridge, although other opening positions are contemplated based on the overall shape of the Reaction Cartridge [34] and Reaction Chamber [16].

However, when low viscosity or sticky material is being vaporized, there is a potential for the concentrate to stick to the area near the opening, away from the Blackbody Substrate [37] and the Heat Envelope [36].

To force the material further into the Reaction Cartridge [34] and closer to the Blackbody Substrate [37] and the Heat Envelope [36], an applicator with a diameter that is smaller than the Reaction Cartridge [34] opening would be necessary.

Alternatively, the user could wait until the temperature within the Reaction Cartridge [34] reached a point wherein the concentrate would become less viscous and sticky.

However, a preferred approach is to use a Reaction Cartridge that includes a mechanism that forces the concentrate toward the Heat Envelope [36].

One embodiment utilizes a spring and plunger system within the Reaction Cartridge [34].

As seen in FIG. 5, a Spring [38] sits at the bottom of the Reaction Cartridge [34], above which sits a Plunger [40], consisting of two sections, the Plunger Post [41] and the Plunger Top [42].

In the embodiment shown, the concentrate is loaded through the bottom of the Reaction Cartridge [34], however, other locations are contemplated.

The Plunger Top [42] fits into the bottom of the Reaction Cartridge [34] and is shaped to fit snugly within the Horizontal plane of the interior.

In this configuration, the Target Point [35] is on the Upper portion of the Reaction Cartridge [34] with the Heat Envelope [36] inside the Reaction Cartridge.

The concentrate is vaporized within the Heat Envelope [36], leaving empty space where the vaporized material was located prior to vaporization.

To move additional concentrate into the Heat Envelope [36], the Spring [38] exerts pressure on the Plunger [40] such that concentrate material is forced toward the Heat Envelope [36].

The Spring [38] will continue to move the Plunger [40] until reaching the top of the Reaction Cartridge [34], which would then be empty of concentrate.

To gauge the efficiency of vaporization as well as knowing the amount of vaporization material remaining in the cartridge, it is preferred that the Vaporizer contain a Viewport that exposes the Reaction Chamber [16] and Vapor Chamber [22].

FIGS. 6A and 6B shows an additional embodiment that uses a Reaction Cartridge Insert [49] to load low viscosity concentrates into the Reaction Cartridge [34].

FIG. 6A is a side cutaway view of the Reaction Cartridge Insert [49] outside and above the Reaction Cartridge [34].

FIG. 6B shows a view of the Reaction Cartridge Insert [49] above the opening in the Reaction Cartridge [34] wherein the Reaction Cartridge Insert [49] is inserted.

The Reaction Cartridge Insert [49] is shaped to fit snugly within the Reaction Cartridge [34] and the top of the Reaction Cartridge Insert [49] acts as a cap, closing the Reaction Cartridge [34] after insertion.

In the embodiment shown, the Reaction Cartridge Insert [49] is loaded from the top, however, the configuration of the Reaction Cartridges Insert [49] and its loading location varies, dependent upon the shape and configuration of the Reaction Cartridge [34].

The Reaction Cartridge Insert [49], in its loaded position, is held in place using pressure from a rubber gasket or a flexible grommet that fits into the loading hole.

An opening in the Reaction Cartridge Insert [49] shown here on the side of the Reaction Cartridge Insert [49] exposing concentrate to the Blackbody Substrate [37] and Heat Envelope [36].

Prior to placing the Reaction Cartridge Insert [49] into the Reaction Cartridge [34], the sticky or viscous concentrate is loaded through the side opening.

It is preferred that the Reaction Cartridge [34] and the Reaction Cartridge Insert [49] are made of a transparent material that would allow a user to see the material within the Reaction Cartridge [34].

FIG. 7 shows left side view of the Vaporizer wherein a Viewport Cover [52] slides toward the User, revealing a Viewport [50]

FIG. 8 shows a cutaway view of the Vaporizer in the closed position. In this configuration, the Vapor Tube [20] is located in the Viewport Cover [52] and extends above the Vapor Chamber [22].

The Vapor Tube [20] has two vapor inlet holes, the Main Vapor Hole [54] and a Forward Vapor Hole [56].

In the closed position, the Forward Vapor Hole [56] is blocked and the Main Vapor Hole [54] is open, allowing the vapor to flow from the Vapor Chamber [22] into the Vapor Tube [20] and out of the Mouthpiece [10].

A Vapor Tube Stopper [48], attached to the Main Housing Unit [12], prevents vapor from entering the forward portion of the Vapor Tube [20], ensuring that the vapor flows efficiently, without being trapped in the Vapor Tube [20] forward portion.

To expose the Viewport [50], the Viewport Cover [52] slides rearward into in an open position, as shown in FIG. 9.

In the open position, the Main Vapor Hole [54] is no longer exposed to the Vapor Chamber [22], but is instead blocked by the Main Housing Unit [12].

The Forward Vapor Hole [56] is now in a position that is exposed to the Vapor Chamber [22].

The Vapor Tube Stopper [48], which is connected to the Main Housing Unit [12] remains in a stationary position. When sliding the Viewport Cover [52], the Vapor Tube Stopper shifts position relative to the Vapor Tube, so that in the open position, the Vapor Tube Stopper [48] resides at the front of the Vapor Tube [20].

The Vapor Tube Stopper [48] also acts a stop point for the Viewport Cover [52] when it slides back, ensuring that the Viewport Cover [52] cannot slide any further.

A number of clear materials can be used for the ViewPort [50], including any transparent solid such as glass or plastic or any contained transparent liquid that can be tinted with a pigment balanced to attenuate the frequency of light being used down to a level that can be safely viewed by the human eye.

The tint should have a minimum optical density of OD 4+ although OD 5+ is recommended. However, the preferred embodiment uses a green polycarbonate, because the green pigment attenuates the chosen light frequency of 445 nm to a safe level and poly-carbonate is strong and resistant to cracking or breaking.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

The invention claimed is:

1. A vaporizer, comprising:
a housing;
a reaction chamber defined within the housing;
a reaction cartridge disposed within the housing and configured to contain a concentrate material for vaporization, the reaction cartridge including a substrate and a reaction cartridge insert configured to position the concentrate material such that the concentrate material is adjacent to the substrate during operation;
a laser diode disposed within the housing; and
a lens aligned with the laser diode such that, during operation, a laser beam generated by the laser diode is directed toward the reaction chamber to heat the concentrate material within the reaction chamber,
the vaporizer being a portable vaporizer configured to receive electrical power via at least one of an internal battery or a wall plug;
wherein the substrate includes a microporous blackbody substrate configured such that, during use, capillary action moves the concentrate material through the microporous blackbody substrate toward a heat envelope.

2. The vaporizer of claim 1, wherein the housing includes a viewport through which a vaporization reaction is viewable during operation.

3. The vaporizer of claim 1, wherein the laser diode is configured to emit a blue laser output.

4. The vaporizer of claim 1, wherein the lens is a single element lens.

5. The vaporizer of claim 1, wherein the housing includes a thermally conductive material.

6. The vaporizer of claim 1, further comprising a power regulator configured to adjust an output power of a laser diode output of the laser diode.

7. The vaporizer of claim 1, further comprising a heat sink attached to the laser diode and to the housing, the heat sink configured to transfer heat, generated by the laser diode during operation, to the housing.

8. The vaporizer of claim 1, wherein the reaction cartridge further includes a spring and a plunger configured to automatically move the concentrate material within the heat envelope of the substrate.

9. A vaporizer, comprising:
a housing;
a disposable reaction cartridge configured to be positioned within the housing and configured to contain a concentrate material for vaporization, the disposable reaction cartridge including a substrate and a reaction cartridge insert configured to position the concentrate material such that the concentrate material is adjacent to the substrate during operation; and
a laser diode assembly disposed within the housing and configured, during operation, to direct a laser beam generated by the laser diode assembly toward the concentrate material,
the vaporizer being a handheld vaporizer configured to receive electrical power via at least one of an internal battery or a wall plug;
wherein the substrate includes a microporous blackbody substrate configured such that, during use, capillary action moves the concentrate material through the microporous blackbody substrate toward a heat envelope.

10. The vaporizer of claim 9, wherein the housing includes a viewport through which a vaporization reaction is viewable during operation.

11. The vaporizer of claim 9, wherein a laser diode of the laser diode assembly is configured to emit a blue laser output.

12. The vaporizer of claim 9, wherein the laser diode assembly includes a single element lens.

13. The vaporizer of claim 9, wherein the housing includes a thermally conductive material.

14. The vaporizer of claim 9, further comprising a power regulator configured to adjust an output power of a laser diode of the laser diode assembly.

15. The vaporizer of claim 9, further comprising a heat sink attached to the laser diode and to the housing, the heat sink configured to transfer heat, generated by a laser diode of the laser diode assembly during operation, to the housing.

16. The vaporizer of claim 9, wherein the reaction cartridge further includes a spring and a plunger configured to automatically move the concentrate material within the heat envelope of the substrate.

* * * * *